United States Patent [19]
Tharpe, Jr. et al.

[11] Patent Number: 6,116,317
[45] Date of Patent: Sep. 12, 2000

[54] APPARATUS HAVING A CORE ORIENTOR AND METHODS OF ORIENTING PORTIONS OF A DISPOSABLE UNDERGARMENT

[76] Inventors: John M. Tharpe, Jr.; Robert M. Herrin, both of 1005 Willie Pitts Jr. Rd. P.O. Box 3970, Albany, Ga. 31706

[21] Appl. No.: 09/020,452

[22] Filed: Feb. 9, 1998

Related U.S. Application Data

[63] Continuation-in-part of application No. 08/667,518, Jun. 21, 1996, Pat. No. 5,879,500.

[51] Int. Cl.$^7$ .................................................. B65G 47/244
[52] U.S. Cl. ................... 156/566; 198/374; 198/377.08; 198/410; 271/185; 414/755
[58] Field of Search ............................. 198/410, 377.04, 198/404, 408, 406, 379, 377.08, 374; 414/755, 757, 776, 777, 782, 783; 156/566; 271/184, 185, 194

[56] References Cited

U.S. PATENT DOCUMENTS

| | | | |
|---|---|---|---|
| 3,269,516 | 8/1966 | Lucas | 198/33 |
| 3,847,273 | 11/1974 | Buhayar | 198/236 |
| 4,726,876 | 2/1988 | Tomsovic, Jr. | 156/552 |
| 4,957,283 | 9/1990 | Kist | 271/90 |
| 5,025,910 | 6/1991 | Lasure et al. | 198/377 |
| 5,282,528 | 2/1994 | Hudson | 198/451 |
| 5,400,574 | 3/1995 | Spatafora | 53/531 |

FOREIGN PATENT DOCUMENTS 404161152  6/1992  Japan .................................. 604/385.2

*Primary Examiner*—Michael W. Ball
*Assistant Examiner*—Gladys Piazza
*Attorney, Agent, or Firm*—Allen, Dyer, Doppelt, Milbrath & Gilchrist, P.A.

[57] ABSTRACT

An apparatus and method for orienting portions of a disposable undergarment, such as a core thereof, is provided. The apparatus preferably includes a core lifting system for lifting a core of a disposable undergarment when in a first orientation position during travel along a predetermined path and a core orientor connected to the core lifting system for orienting the core in a second orientation position along the predetermined path of travel. The core orientor preferably includes at least one drive for driving the core lifting system along the predetermined path of travel and an orientation changing system associated with the at least one drive for changing the orientation of the lifted core to the second orientation position when driving at least portions of the core lifting system along the predetermined path of travel.

38 Claims, 8 Drawing Sheets

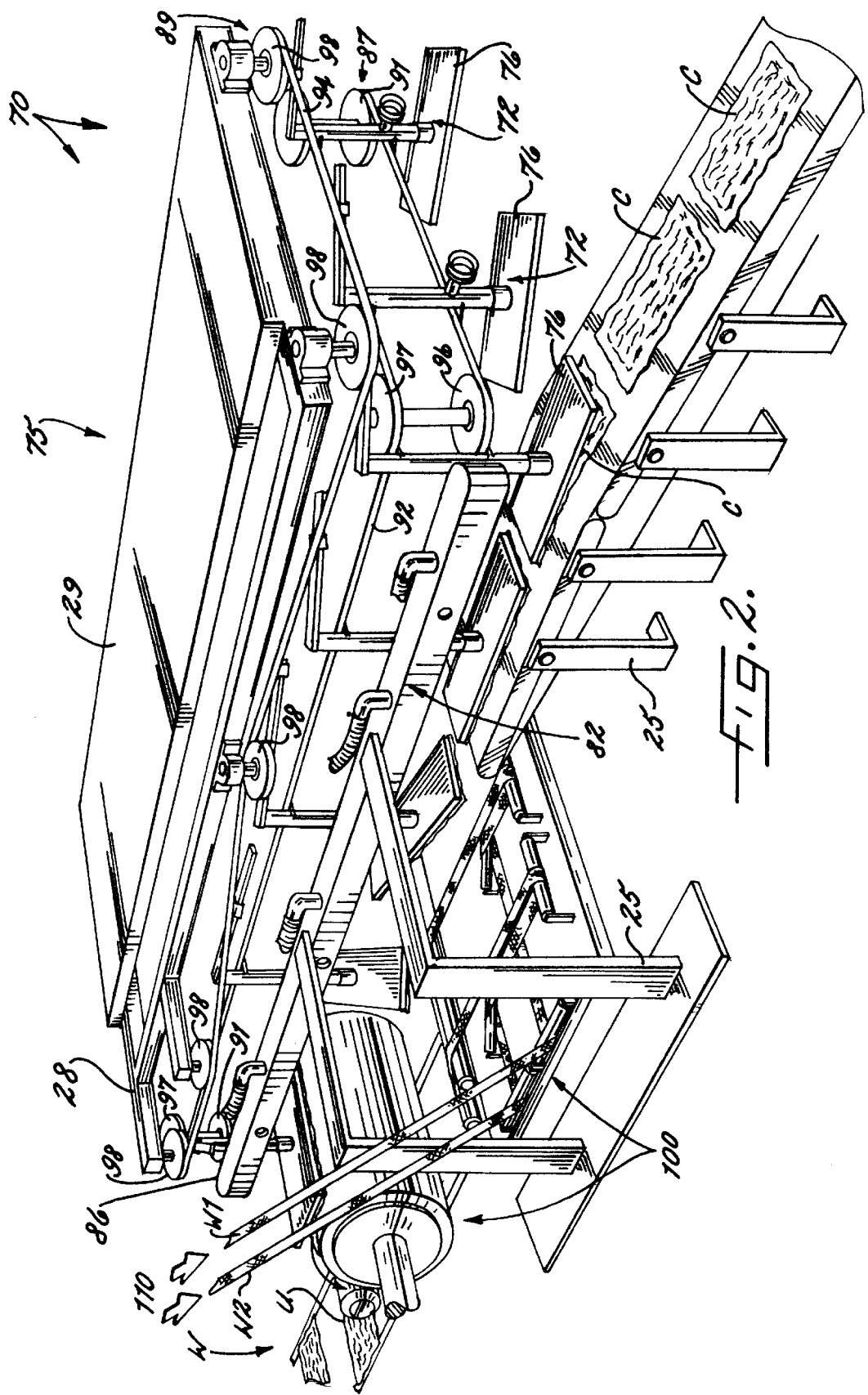

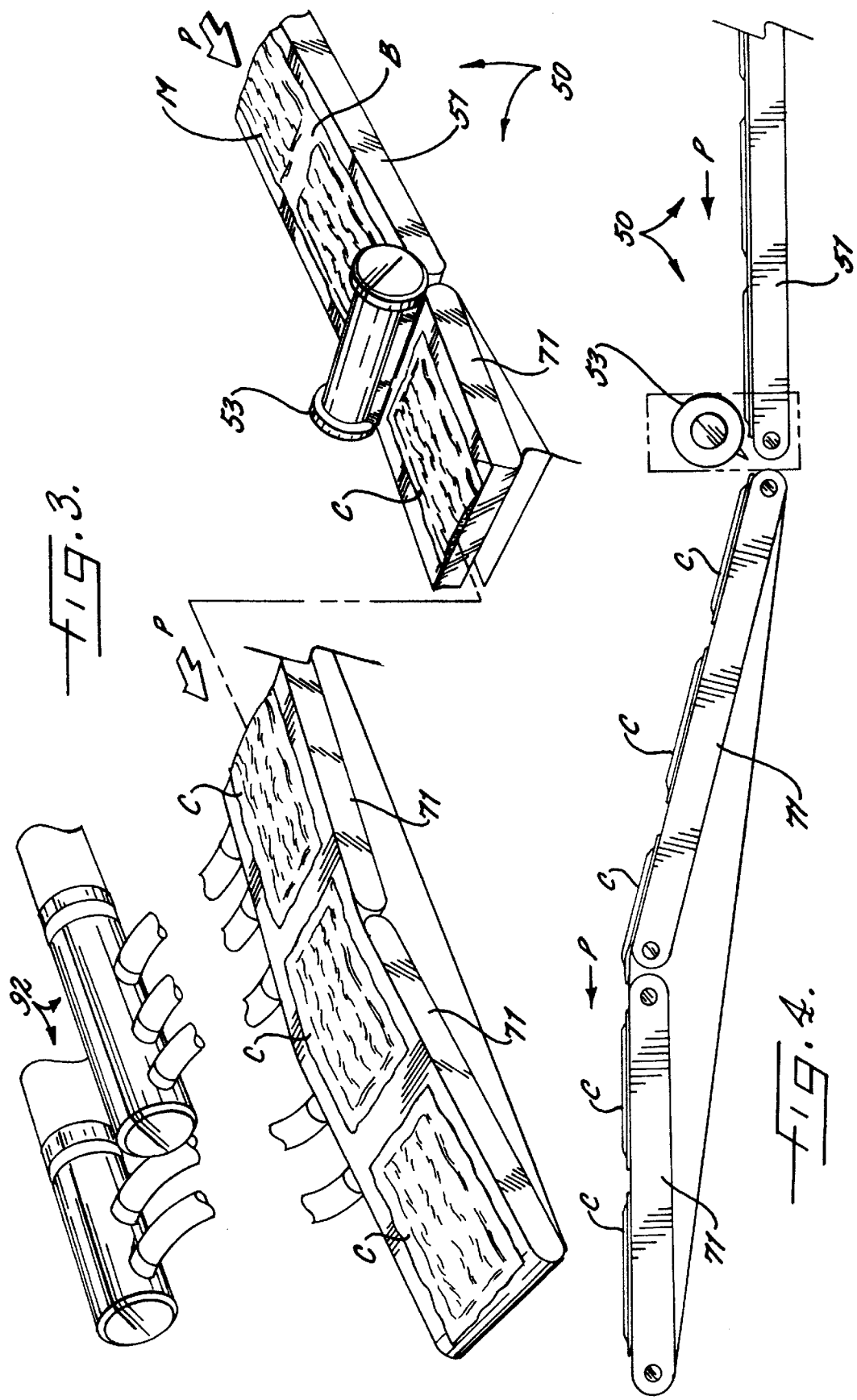

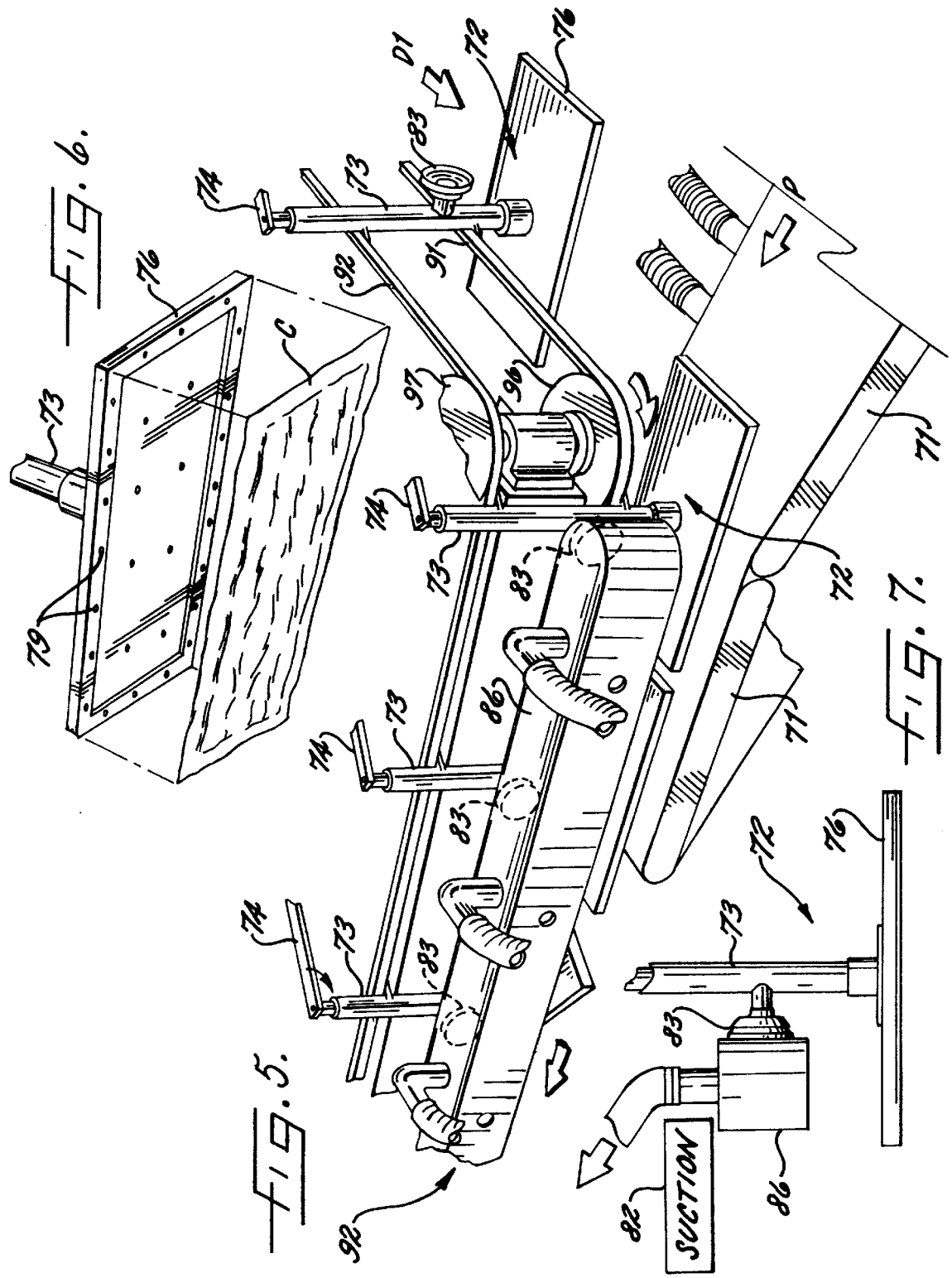

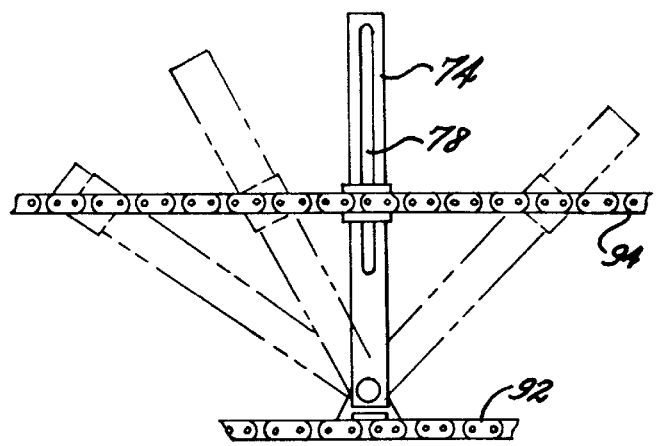
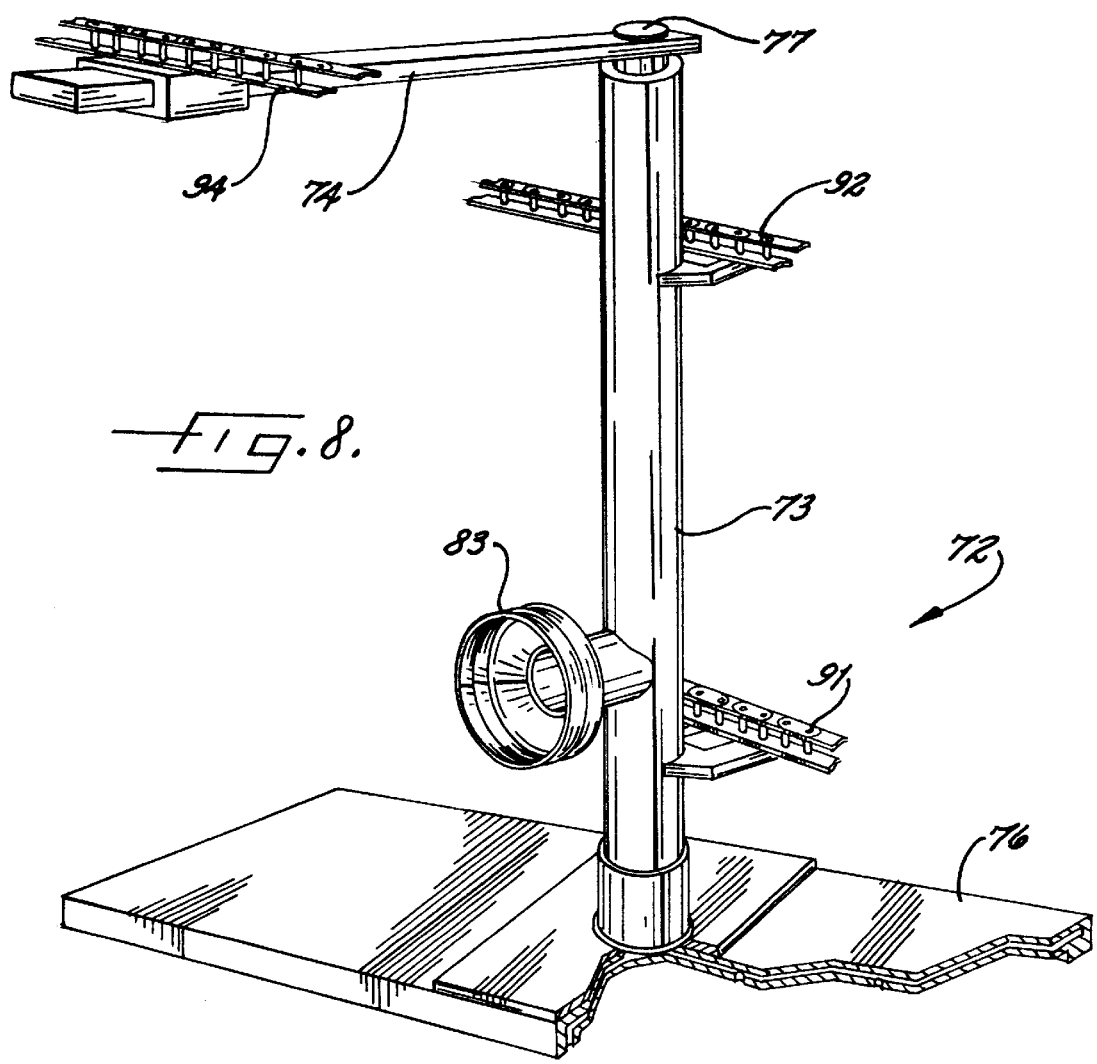

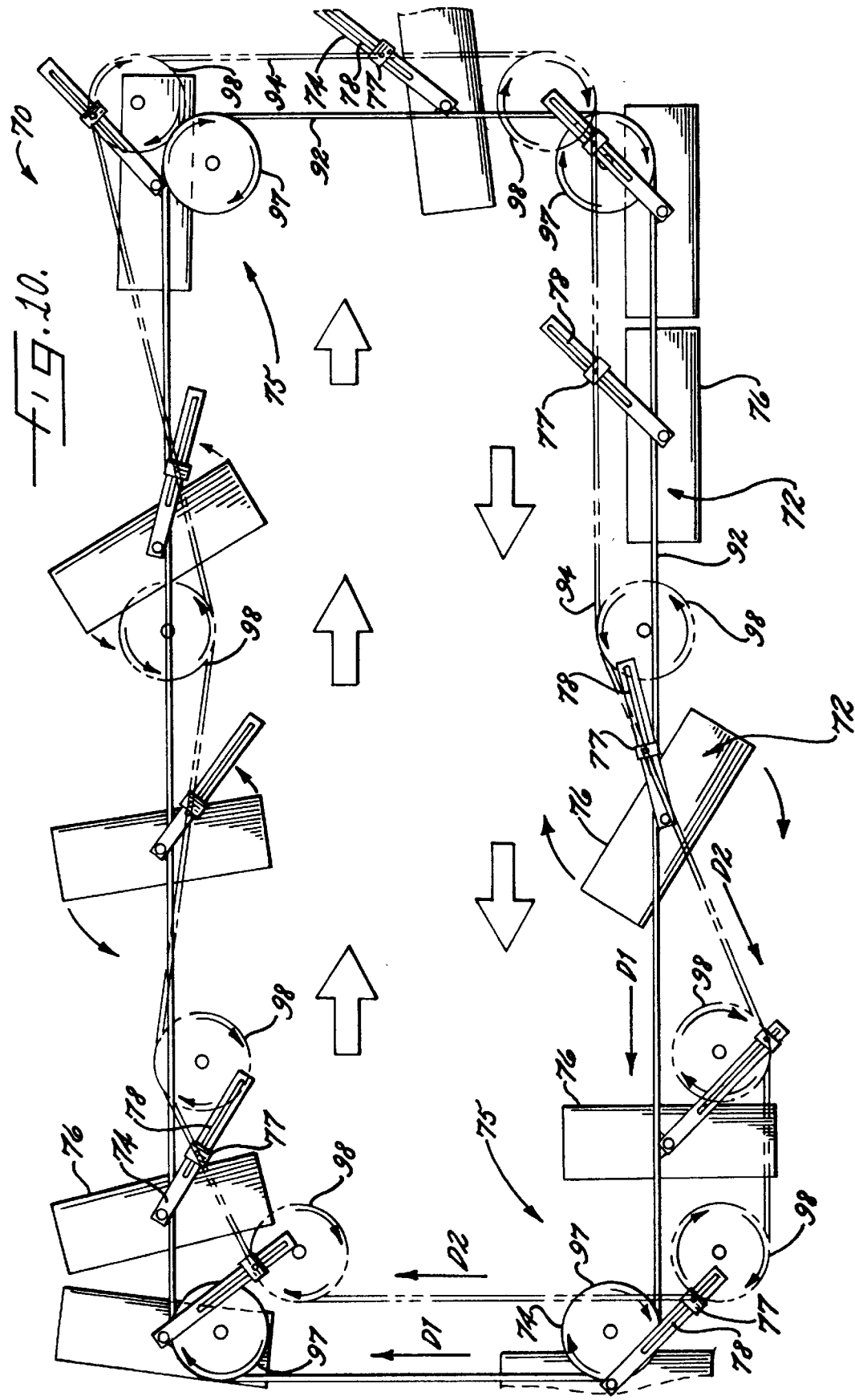

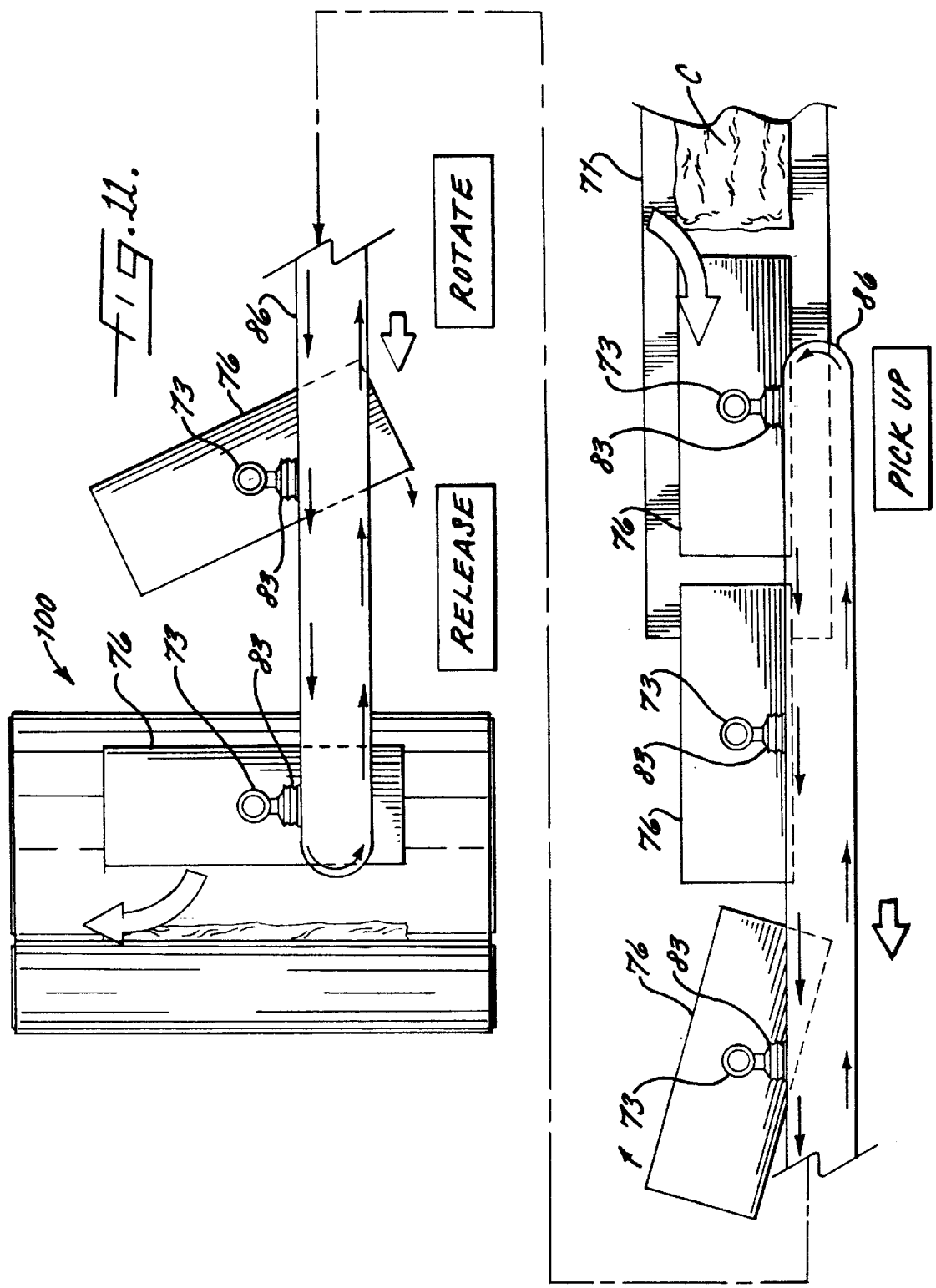

APPARATUS HAVING A CORE ORIENTOR AND METHODS OF ORIENTING PORTIONS OF A DISPOSABLE UNDERGARMENT

RELATED APPLICATIONS

This patent application is a continuation-in-part of U.S. patent application Ser. No. 08/667,518; filed on Jun. 21, 1996 U.S. Pat. No. 5,879,500 and which is incorporated herein by reference in its entirety.

FIELD OF THE INVENTION

The invention relates to the field of disposable products, and, more particularly, to the field of disposable undergarments.

BACKGROUND OF THE INVENTION

Over the years, consumers have shifted demand from cloth diapers to disposable diapers for infants and toddlers. This demand has increased and developed the disposable diaper industry into a major industry. As this industry developed, consumers preferred and often demanded improvements in disposable products which included better core absorbency, products which are easier to fasten, detach, and reattach side peripheries of the waistbands, various sized of products for various weights and sizes of infants and toddlers, and better control of leakage from around the legs and waistbands when the diaper is positioned on an infant or toddler.

This development of the disposable diaper industry, however, has increased demand for faster and more efficient disposable undergarment production. This demand is further complicated by the development of disposable infant and toddler briefs, which have a different product configuration and have different product performance requirements than disposable diapers. Also, because of the relative success of the disposable diapers and the high volume of disposable diaper products produced in manufacturing, the market for toddler briefs has generally been a much smaller subset of the infant and toddler disposable diaper market. The demand for toddler briefs in general is substantially less than the disposable diapers. Accordingly, these specially configured briefs are not normally produced on the same production line as the disposable diaper production line. Because the market demand for these briefs is less, product manufacturers are less inclined to invest in additional machinery for producing these products. The product manufacturer, however, is also pushed by retailers and consumers to provide a full-line of disposable products for infants and toddlers.

Additionally, as the nursing home care and elderly care industry has grown over the years, the elderly often have needed more and more assistance from nursing home or elderly care personnel, including urination and bowel movement assistance. Urination and bowel movement problems have also arisen among various aged adults such as loss of bladder control through childbirth or other medical reasons. Therefore, because manufacturers of disposable undergarments can be limited in the foot-print or square footage of floor space available for production, especially for adult, toddler, and infant specialty undergarments such as briefs, and because labor costs can be quite expensive, demand continues to increase for systems which increase production speed of disposable undergarments in a relatively small amount of space.

SUMMARY OF THE INVENTION

In view of the foregoing background, the present invention advantageously provides a disposable undergarment forming apparatus and method which produces a plurality of undergarments by orienting a portion of the undergarment, such as the core, the waistband, the leg gathers, the backsheets, or the respective portions thereof, form a first orientation position along a predetermined direction of travel to a different second orientation position along the same predetermined direction of travel. The present invention also advantageously provides a disposable undergarment forming apparatus and method of producing a plurality of disposable undergarments which increases the production speed and reduces the square footage of floor or manufacturing space needed for producing the disposable undergarments to thereby increase the value and productivity of a production line.

The present invention additionally advantageously provides a disposable undergarment forming apparatus and method for producing disposable undergarments more efficiently. The present invention further advantageously provides a disposable undergarment forming apparatus and method having the flexibility to produce both infant or toddler undergarments and adult undergarments and produce different undergarment configurations efficiently with only minor production line changes. The present invention still further provides an apparatus and method for orienting a portion of a disposable undergarment, such as the core, the waistband, a leg gather, or respective portions thereof, from a first orientation position along a predetermined direction of travel to a different second orientation position along the same predetermined direction of travel.

More particularly, the apparatus preferably includes lifting means for lifting a portion of a disposable undergarment when in a first orientation position during travel along a predetermined path and orienting means connected to the lifting means for orienting the portion of the disposable undergarment in a second orientation position along the predetermined path of travel. The orienting means preferably includes driving means for driving the lifting means along the predetermined path of travel and orientation changing means associated with the driving means for changing the orientation of the lifted portion of the disposable undergarment to the second orientation position when driving the lifting means in the predetermined path of travel. The orientation changing means, for example, preferably includes means for driving portions of said lifting means along first and second driving paths. The second driving path is preferably positioned to generally overlie the first driving path and to direct a second portion of the lifting means along a different path of travel than a first portion traveling along the first driving path.

According to another aspect of the present invention, an apparatus is provided for orienting a plurality of cores of a web of a plurality of disposable undergarments. The apparatus preferably includes lifting means for lifting each of a plurality of cores for forming a web of disposable undergarments when in a first orientation position during travel along a predetermined path and core orienting means connected to the lifting means for orienting each of the plurality of cores in a second orientation position along the predetermined path of travel. The core orienting means preferably includes driving means for driving the lifting means along the predetermined path of travel and orientation changing means associated with the driving means for changing the orientation of each of the lifted cores to the second orientation position when driving the lifting means along the predetermined path of travel. The orientation changing means, for example, preferably includes means for driving portions of the lifting means along first and second driving paths. The second driving path is preferably positioned to generally overlie the first driving path and to direct a second portion of the lifting means along a different path of travel than a first portion traveling along the first driving path.

The present invention also advantageously provides methods for orienting a portion of a disposable undergarment such as a core, a waistband, a leg gather, a backsheet, or respective portions thereof. A method preferably includes lifting a portion of a disposable undergarment by a lifter when in a first orientation position during travel along a predetermined path and orienting the portion of the disposable undergarment in a second orientation position along the predetermined path of travel by driving the lifter along the predetermined path of travel and changing the orientation of the lifted portion of the disposable undergarment to the second orientation position when driving the lifter along the predetermined path of travel.

Because the core of a disposable undergarment can require extensive forming, preparing, and handling operations, e.g., due to the absorbency or super-absorbency nature of the core of a disposable undergarment, the apparatus and method of the present invention can advantageously be and is preferably used for orienting a core of a disposable undergarment. Accordingly, another method of the present invention preferably includes lifting a core of a disposable undergarment by a core lifter when in a first orientation position during travel along a predetermined path and orienting the core in a second orientation position along the predetermined path of travel by driving the core lifter along the predetermined path of travel and changing the orientation of the lifted core to the second orientation position when driving the core lifter along the predetermined path of travel.

Further, because it is generally desirable to produce a large quantity, e.g., hundreds, thousands, or tens of thousands, of disposable undergarments rapidly, efficiently, and in a smaller square-footage of manufacturing floor space, yet another method for orienting a plurality of cores of a web of disposable undergarments is advantageously provided according to the present invention. Yet another method preferably includes transporting each of the plurality of cores along a predetermined path of travel when in a first orientation position, lifting each of the plurality of cores by one of a plurality of lifters when each of the plurality of cores are in the first orientation position during travel along a predetermined path, and orienting each of the plurality of cores in a second orientation position along the predetermined path of travel by driving the lifter along the predetermined path of travel and changing the orientation of each of the lifted cores to the second orientation position when driving each of the plurality of lifters along the predetermined path of travel.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 2 is a perspective view of a core orienting apparatus according to the present invention;

FIG. 3 is a fragmentary perspective view of a conveyor conveying a plurality of individual cores of a corresponding plurality of disposable undergarments along a predetermined direction of travel of a core orienting apparatus after being individually separated from a sheet of a plurality of cores according to the present invention;

FIG. 4 is a side elevational view of a conveyor conveying a plurality of individual cores of a corresponding plurality of disposable undergarments along a predetermined direction of travel of a core orienting apparatus after being individually separated from a sheet of a plurality of cores according to the present invention;

FIG. 5 is a fragmentary perspective view of a core orienting apparatus being positioned for pick-up of each of the plurality of individual cores by a platen having a vacuum associated therewith according to the present invention;

FIG. 6 is an exploded perspective view of a platen of a core orienting apparatus positioned to pick-up or release an individual core according to the present invention;

FIG. 7 is a front elevational view of a platen of a core orienting apparatus being positioned for vacuum or suction of a core during pick-up according to the present invention;

FIG. 8 is a fragmentary perspective view of a core lifter connected to a drive of a core orientating apparatus according to the present invention;

FIG. 9 is a pivotable and slidable arm of a core lifter connected to a drive of a core orienting apparatus according to the present invention;

FIG. 10 is a top plan view of a core orienting apparatus according to the present invention;

FIG. 11 is a top plan view of a pick-up and release of a plurality of individual cores of a core orienting apparatus according to the present invention.

DETAILED DESCRIPTION OF A PREFERRED EMBODIMENT

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like number refer to like elements throughout, and prime and double prime notation where used indicate similar elements in alternative embodiments.

Figure 1:
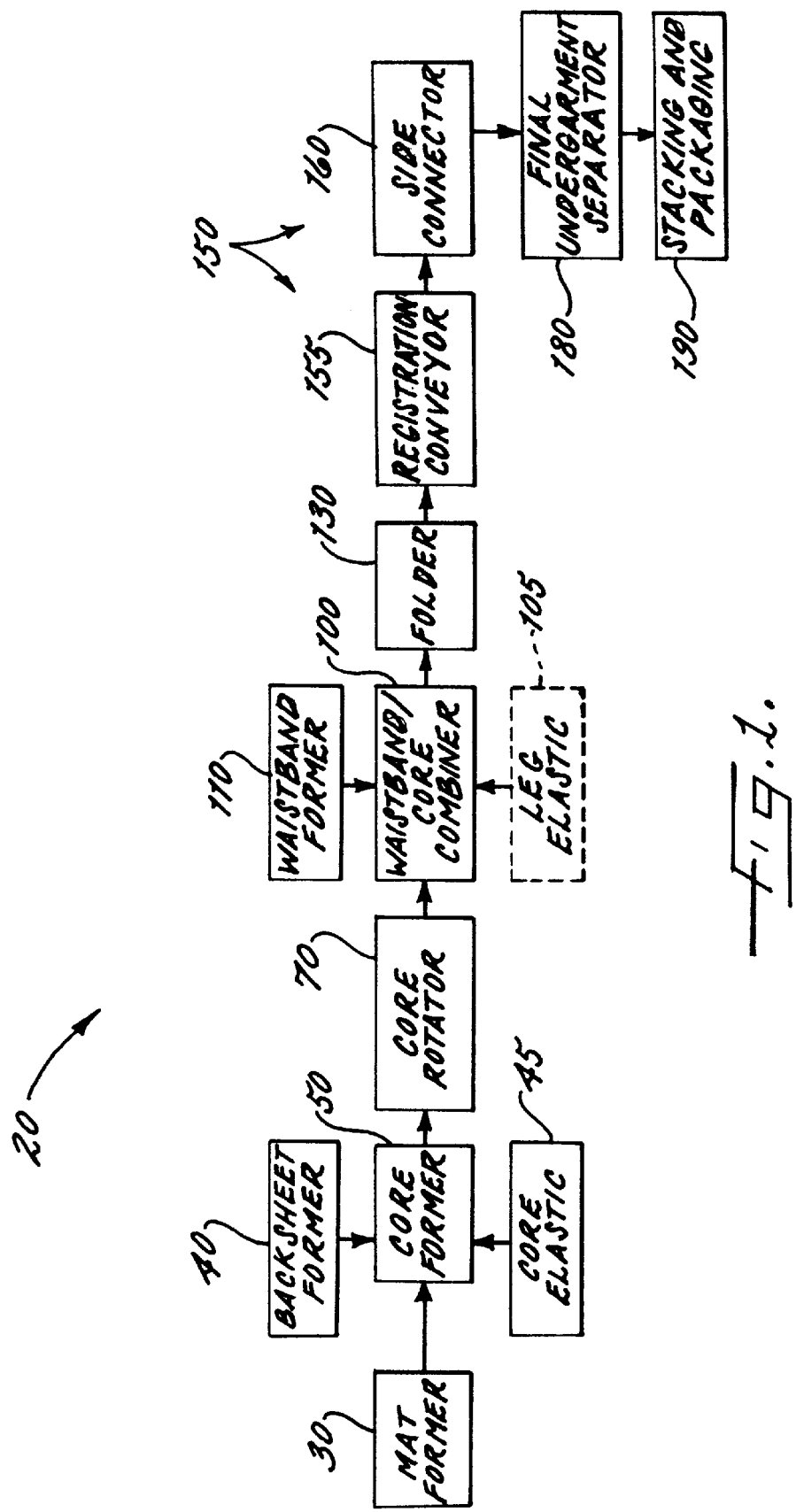
FIG. 1 is a schematic block diagram of an apparatus and method for forming a disposable undergarment having a core orientor associated therewith according to the present invention.
Figure 12:
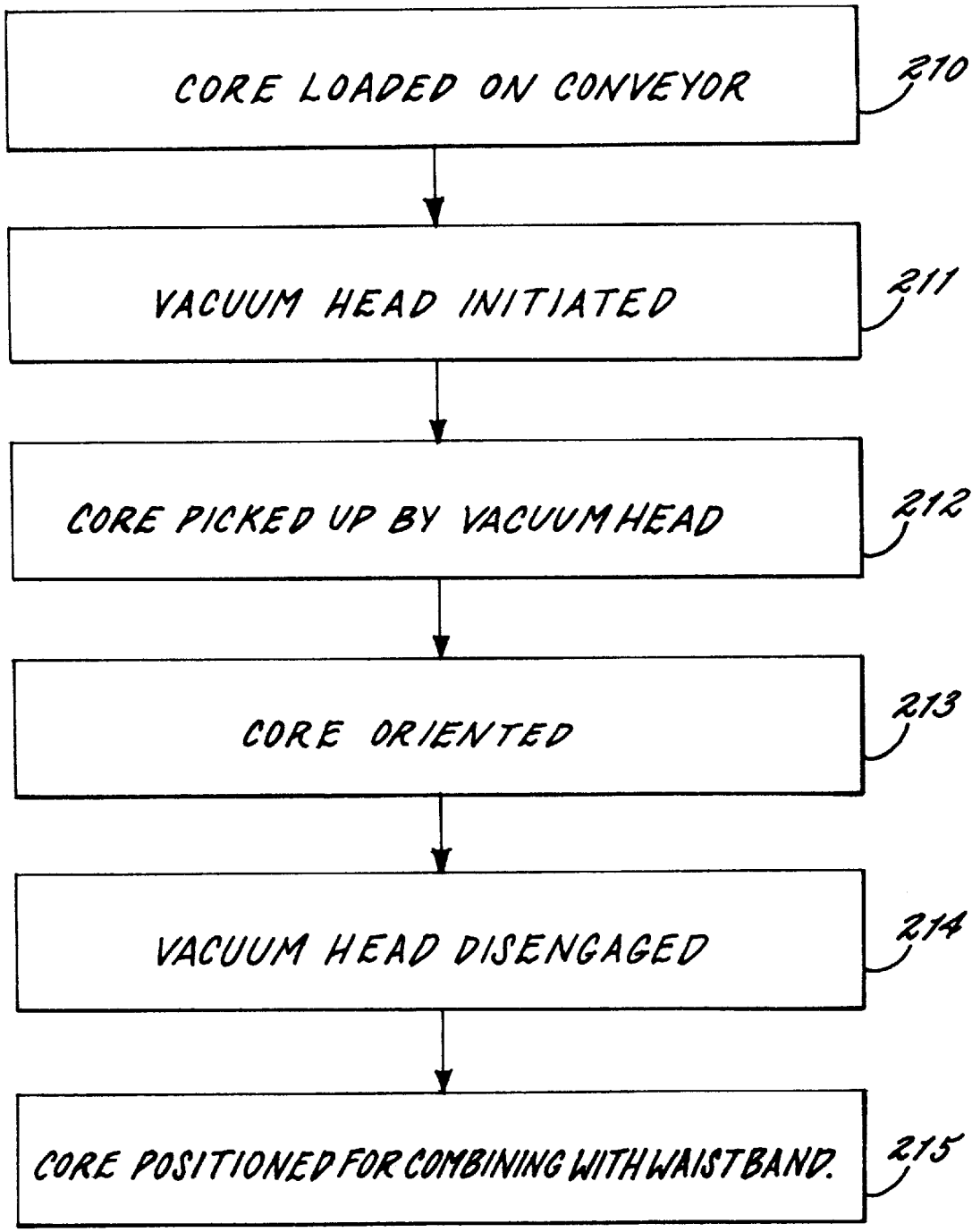
FIG. 12 is a schematic block diagram of an operational method of a core orienting apparatus according to the present invention.

FIG. 1 schematically illustrates an overview of a disposable undergarment apparatus 20 and method for forming a plurality of disposable undergarments according to the present invention. FIG. 1 will be referenced throughout this description as an overview for other more specific elements and operational aspects described throughout. The apparatus 20 preferably includes a frame 25 (see portions thereof illustrated in FIG. 2), including a plurality of frame members, and core forming means, e.g., a core former 50, mounted to the frame 25 for forming a stream or a sheet S of a plurality of elongate undergarment cores C traveling along a path of travel P generally indicated by the flow arrows (see FIGS. 3–4 and 7). The cores C, as well as other portions of undergarments U, preferably are conveyed or driven along the path of travel P by various conveyors 51, 71 which include respective conveyor drives of the apparatus 20 as understood by those skilled in the art. The apparatus 20 preferably also includes control means, such as one or more controllers, connected to the conveyors 51, 71 and the various other portions of the apparatus 20 described further herein for controlling various stages of the undergarment forming apparatus 20 during the formation and production of undergarments U. The controllers, e.g., controllers 162, 192, preferably are microprocessor or other computer based controls and can include a plurality of optical encoders as understood by those skilled in the art.

As illustrated in FIG. 1, mat forming means, e.g., a mat former 30, is positioned upstream from the core forming means 50 for forming a mat M for each of the cores C produced by the apparatus 20. The mat former 30, as understood by those skilled in the art, preferably includes a feed for feeding a super absorbent polymer ("SAP") and a pulp source. The pulp source preferably includes rolled pulp mounted on pulp feed rolls and a pulp grinder for grinding the pulp. The SAP and pulp are fed to a forming chamber where the pulp is mixed with the SAP to form a stream or continuous flow of bulked mat material at a mat material former. The mat material of the mat M forms a significant part of the core C of an undergarment and assists in forming an absorbent portion of the core C for collecting moisture such as urination form and adult or infant. A sheet of tissue from a tissue source is preferably positioned to underlie the bulked mat material, and the combination is conveyed by a debulking conveyor to a debulker. The tissue can also be positioned to underlie the mat material and wrapped around, e.g., so as to overlie, the mat material as well. From the debulker, the debulked stream of mat material is embossed by an embosser and cut into a plurality of individual mats M by a mat knife or mat separator positioned downstream from the embosser.

The individual mats M are then intermittently-spaced and conveyed by a conveyor along the path P of travel to the core forming means 50. The core forming means 50 of the apparatus 20 preferably includes mat securing means, e.g., a mat/backsheet combiner, for securing a lower surface of each of the plurality of intermittently-spaced elongate undergarment mats M to an upper surface of a sheet S, e.g., backsheet B, of a polymeric material traveling along the path of travel P so that side lengthwise peripheries of the intermittently-spaced elongate undergarment mats M are positioned generally parallel to side lengthwise peripheries of the polymeric sheet B (see also FIGS. 3–4). The polymeric core backing sheet B is preferably supplied by a sheet source or backsheet former 40 such as a wound roll of the polymeric sheet material mounted on feed rolls. The undergarment mats M are preferably secured to the polymeric backing sheet B by an adhesive material such as glue from an adhesive applicator. Such adhesive applicators as described and referenced in various positions herein will be understood by those skilled in the art.

Core elastic applying means, e.g., a core elastic applicator 45 (FIG. 1), is positioned downstream from the mat securing means for applying strips of elongate elastic material to the upper surfaces of the side lengthwise peripheries of the polymeric sheet B adjacent and generally parallel to the intermittently-spaced elongate undergarment mats M. The core elastic applicator 45 preferably includes a source of core elastic, a feeder for feeding the core elastic to the polymeric backing sheet B, and an adhesive applicator for applying adhesive to either the backing sheet or the core elastic to thereby secure the core elastic to the backing sheet B.

The core forming means 50 can also further include stand-up leg gather forming means, e.g., a stand-up leg gather ("SULG") former, positioned adjacent the core elastic applying means for forming stand-up leg gathers on the polymeric sheet B, as understood by those skilled in the art, which inhibit liquid, such as from urination, from leaking from the legs of the undergarment U. Although various single-piece, three-piece, and other configurations of a SULG, as understood by those skilled in the art, can be formed by the apparatus 20 for the present invention, the stand-up leg gather forming means according to the present invention preferably includes leg sealing means, e.g., a sealer, for sealing polymeric material so as to form a liquid impervious seal around each of the SULGs of the plurality of cores C. The sealer preferably is an adhesive or heat seal applied between the layers of polymeric material. The seal, e.g., heat or adhesive, is preferably formed between the SULG polymeric material and the polymeric backing sheet B to inhibit leakage of moisture or liquid from and around the mat material and legs.

The SULGs, for example, can be formed by a first sheet of polymeric material supplied form a SULG polymeric sheet source, a plurality of elongate elastic strips supplies from a SULG elastic source, and a top sheet of non-woven material supplied from a top sheet non-woven sheet source. The sheet of SULG polymeric material is divided into two strips, one for each leg. A first set of strips. e.g., one or more strips, of elastic material is positioned to extend adjacent a lengthwise side periphery of the backing sheet B, and each strip of polymeric material is positioned to overlie the first set of elastic strips and extend between the lengthwise side periphery and the mat material. The seal between the polymeric sheet material as described above is formed.

The non-woven sheet material overlies and adheres to the polymeric material along each leg, but also overlies the mat material of the core C. A second set of elastic strips, e.g., one or more elastic strips, are also positioned along peripheries of each of the SULG polymeric strips adjacent the mat material. These elastic strips preferably are positioned between the non-woven sheet material and the polymeric strip. These first and second sets of elastic strips preferably are applied to the surface of the backing sheet B in an extended position so that when the strips are relaxed or retracted, the backing sheet B, the SULG polymeric strips, and the non-woven sheet gather or form gathers extending lengthwise along what will become the legs of the core C. This, for example, allows the SULGs which eventually become the SULGs of the undergarments to be stretched when positioning the undergarment on a user to thereby provide a snug and comfortable fit around the legs of a user when relaxed or retracted. The portion of the SULG polymeric strips, the second set of elastic strips, and the portion of the non-woven sheet adjacent lengthwise peripheries of the mat material are formed to extend upwardly away from the upper surface of the mat material and the backing sheet as illustrated.

The core forming means 50 also includes first separating means, e.g., a core separator 53 such as a knife or blade illustrated in FIGS. 3–4, positioned downstream from the core elastic applying means for separating the stream of intermittently-spaced elongate undergarment cores C into a plurality of individual undergarment cores C. The core separator 53 preferably is a knife mounted to a drum cylinder or roll having a predetermined circumference and which overlies and periodically contacts the stream of cores C. The knife extends the length or height of the drum cylinder so as to form a relatively small cutting line. The drum cylinder is mounted to rotate so that during one rotation cycle the knife cuts the stream of cores C only one time to thereby produce a plurality of individual cores C during a corresponding plurality of rotations. It will be understood by those skilled in the art, however, that other core separator 53 configurations could be used as well as multiple blades on a larger drum cylinder.

Additionally, as best illustrated in FIGS. 2–12, the apparatus 20 also includes an orienting apparatus 70 for orienting a plurality of portions, e.g., cores, waistbands, leg gathers, backing sheets, or respective portions thereof, of web of a plurality of disposable undergarments. Because the core C of a disposable undergarment can require extensive forming, preparing, and handling operations, e.g., due to the absorbency or super-absorbency nature of the core of a disposable undergarment as described herein above, the orienting apparatus 70 of the present invention can advantageously be and is preferably used for orienting a core C of a disposable undergarment. The orienting apparatus 70 preferably includes lifting means for lifting each of a plurality of cores C for forming a web W of disposable undergarments when in a first orientation position during travel along a predetermined path P or direction of manufacture and orienting or core orienting means connected to the lifting means for orienting each of the plurality of cores in a second orientation position along the predetermined path of travel P. The core orienting means preferably includes driving means for driving the lifting means along the predetermined path of travel P and orientation changing means associated with the driving means for changing the orientation of each of the lifted cores C to the second orientation position when driving the lifting means along the predetermined path of travel P. The orientation changing means, for example, preferably includes means for driving portions of the lifting means along first and second driving paths D1, D2. The second driving path D2 is preferably positioned to generally overlie the first driving path D1 and to direct a second portion of the lifting means along a different path D2 of travel than a first portion traveling along the first driving path D1 (see FIGS. 2, 5, and 10).

The orienting apparatus 70, e.g., including a core orientor 80, is preferably positioned downstream from the core forming means 50 for orienting, e.g., preferably by rotating each core C about 90 degrees, each of the plurality of individual elongate undergarment cores C to a position having a lengthwise extent of the cores C transverse the path of travel P. The core orientor or rotator 70 preferably lifts the individual cores C from the surface of the conveyor 71, orients by rotating each of the cores C to a position transverse the path of travel P, and then releases each of the cores C for other downstream operations. The lifting of each of the cores C is preferably performed by a vacuum or suction system 82 which defines core holding means for holding a core C in a suspended position after lifting the core C off of a surface and for releasing the core C from the suspended position and can operatively accommodate the lifting and rotating of a plurality of cores C and inoperatively release the cores C therefrom so that the production line operation continues in a smooth process.

The vacuum or suction system 82 preferably includes a vacuum chamber forward in a suction delivery channel 86 having a vacuum source connected thereto by a plurality of hoses 87 and a plurality of core lifters or lifting members 72 arranged so that a suctioning interface member 83, a flexible suction cup or annular flexible flange, of each of the core lifters or lifting members 72 abuttingly contact and are in fluid communication with the vacuum chamber 86. The vacuum chamber 76 provides the vacuum lift or holding means for each of the plurality of lifters 72 when the lifters 72 are in contact with the vacuum chamber 86.

The plurality of lifters 72 preferably are mounted to drive means 75, e.g., a pair of closed-loop chain drives 91, 92, a plurality of drive gears 96, 97 for contactingly driving each of the pair of chain drives, and at least one motor 95 for driving each of the plurality of drive gears 96, 97, so as to rotate around the first and second drive path D1, D2. Each lifting member 72 includes a pair of mounting arms 73, 74 connected to the drive means and a core plate member or platen 76 mounted to one 73 of the pair of mounting arms 73, 74. The platen 76 preferably is arranged to be positioned so as to overlie an individual core C for lifting and abuttingly contacting the core C for orientation when the suction interface member 83 contacts and is in fluid communicating with the vacuum chamber 86. A first arm 73 is connected to the platen 76 and has a second arm 74 pivotally or rotatingly connected thereto. The second arm 74 has an end thereof which pivotally connects to the first arm 73 and extends outwardly therefrom.

The first arm 73 is also somewhat fixedly connected to a first portion of the driving means, e.g., a first chain drive 87. The second arm 74 is slidably and pivotally connected to a second portion of the driving means, e.g., a second chain drive 89. The first and second chain drives 87, 89 are also mounted to portions 28, 29 of the frame 25. The second chain drive 89 also preferably includes a drive chain 94, a plurality of gears 98 drivingly connected to the drive chain 94, and at least one motor or a connection to the other motor for driving the gears 98.

The second arm 74 also advantageously includes an elongate slot 78 positioned to receive a slot following pin 77 therein. The pin 77 connects to the second chain drive 89 and slides along or follows the slot 78 when the lifter 72 moves along the first and second drive paths D1, D2 as best illustrated in FIG. 10. This structure, in essence, defines an adjustable compensating means for compensating for the differences in the drive paths D1, D2 which provide orientation or rotation of the platen 76 of each of the lifters 72. In other words, the slidable movement of the following pin 77 within the slot 78 of the second arm 74 assists during the slowing down of the movement of the pin in comparison to the constant movement of the first arm and platen along the first drive path by the changing of the phase angle based upon the sine or cosine (see FIG. 10). The second chain drive is preferably positioned for driving the second arm 74 along a different path of travel than the first chain drive which drives the first arm 73 along a predetermined path of travel. Notably, as illustrated in FIG. 10, the lifters 72 continuously travel along a closed loop path of travel when being driven by the first and second chain drives 87, 89.

As perhaps best illustrated in FIGS. 5–9 and 11, the first arm 73 of each of the plurality of lifters 72 preferably includes a substantially hollow interior portion extending a selected length of the first arm. The platen 76 also has a plurality of openings 79 formed therein and positioned in fluid communication with the substantially hollow portion of the first arm 73 connected thereto. The suctioning interface member 83 is connected to the first arm 73 and also in fluid communication with the substantially hollow portion of the first arm 73. When suction or a vacuum is applied to the suctioning interface member 83 when each lifter 72 travels along the predetermined path adjacent the conveyor 71, the suction extends through the suctioning interface member 83 from the elongate vacuum or suction delivery channel 86, e.g., by slidable engagement with the opening of the channel 86, through the substantially hollow interior portion of the first arm 73, and through the plurality of openings 79 in the platen 76 for lifting a core C when positioned on a surface of the conveyor 71 adjacent the platen 76. The conveyor 71 also can have a vacuum or suction from the vacuum or suction system 82 applied thereto for assisting in inhibiting slippage or movement of the cores C positioned thereon (see FIGS. 3 and 5).

Each lifter or lifting member 72 is arranged for rotating the core C from the position having a lengthwise extent travelling in the direction of the path of travel P to the position transverse the path of travel P. Upon reaching a predetermined position, the lifting member 72 releases the core C and continues to rotate around the first and second drive paths D1, D2 so as to return for lifting another core C in the production process.

The orienting or rotating of the cores C so as to have lengthwise extents transverse the path of travel P allows for the disposable undergarment forming apparatus 20 to have a reduced number of and a more narrow glue or adhesive application path for one or more glue or adhesive applicators to secure the waistbands to the cores C downstream. The glue or adhesive is preferably applied before rotation of the cores C. It can also allow for a reduced amount of adhesive to be used for each undergarment and thereby reduce the production costs associated with each undergarment.

Elastic waistband forming means, e.g., a waistband former 110, preferably is positioned adjacent the core rotating means 50 and positioned to form at least two continuous strips of elongate elastic material extending along the path of travel P for forming elongate elastic waistbands W1, W2. The waistband forming means preferably is formed "off-line" from the path of travel P for ease of modifying the type of waistband that can be used for a given product. It will be understood by those skilled in the art, however, that the waistband forming means 110 can also be positioned "in-line" as well. The waistband forming means 110 includes dividing means, e.g., a sheet divider as understood by those skilled in the art, for dividing a continuous sheet of non-woven material supplied from a non-woven sheet source into the plurality of continuous strips and strip combining means, e.g., a strip combiner, for combining strips of elastic material from a waistband elastic supply source with the plurality of continuous strips of non-woven material.

The plurality of continuous strips as described above preferably includes four strips of non-woven material. These four strips form two pairs of continuous waistband strips. Each waistband strip has an upper and lower non-woven strip and one or more, e.g., preferably four, elastic strips positioned therebetween. Two of the four non-woven strips preferably have greater widths than the other two non-woven strips. These two greater width non-woven strips preferably form the lower non-woven strips of the two pairs of continuous waistband strips. The one or more elastic strips preferably are only adhered to a medial portion of the lower non-woven strips so that lengthwise periphery portions of the lower non-woven strips remain unelasticized. After the upper and lower non-woven strips and the elastic strip(s) are combined, one of the non-elasticized lengthwise periphery portions of each upper non-woven strip is folded by a folding guide member so as to now overlie and adhere to at least lengthwise peripheries of the upper non-woven strip. This fold, for example, will provide a smooth closure or sealed surface to the waistband strips and will eventually downstream become the lower portion of the waistband of the undergarment as described further herein.

The one or more elastic strips preferably are adhered to and positioned between the upper and lower non-woven strips, as well as the waistband strips being adhered to the individual cores as described further herein, in an extended position so that when released to the retracted or relaxed position, the waistband strips have a plurality of gathers formed therein. This, for example, allows the waistband strips which eventually become the waistbands for the undergarments to be stretched when positioning the undergarment on a user to thereby provide a snug and comfortable fit to the waist of a user when retracted or relaxed.

Combining means, e.g., waistband/core combiner 100, is positioned downstream from the core forming means 50 and is positioned to receive the two continuous waistband strips of elongate elastic material from the elastic waistband forming means 110 along the path of travel P for respectively combining each of the two elongate elastic strips of material so as to be secured to, e.g., by using a glue or other adhesive, the respective side peripheries, e.g., lateral or widthwise sides, of each of the plurality of individual undergarment cores C traveling transverse to the path of travel to thereby from a chain of a plurality of undergarments U joined by the elongate elastic waistbands W1, W2. The combiner 100 preferably includes a plurality of feed and/or draw rolls positioned to cooperate with a conveyor which conveys the transversely positioned cores along the path of travel P. The rolls preferably feed or draw the waistband and, optionally, leg elastic to combine with the cores.

The lateral or widthwise peripheries of each individual core C preferably is glued or adhesively applied to the space-apart pair of waistband strips of the combiner. The lateral peripheries of each core C preferably are initially secured to the waistband strips so as to overlie the waistband strips. As will be described further herein, the greater widthwise lower strips of the waistband strips are later folded so that portions of what was designated as the lower non-woven strip now overlie the lateral side peripheries of the core and what was designated as the upper non-woven strip.

A leg elastic source 105, according to another embodiment of the present invention, can supply additional leg elastic at this stage of the production process, or further upstream, for combining with and into the waistband/core combiner 100. The leg elastic is preferably adhered to the lengthwise peripheries of each of the plurality of cores adjacent the SULGs in an extended position so that when the leg elastic is released to a retracted or relaxed position gathers are formed around these lengthwise peripheries. This, for example, allows the leg gathers which eventually become the legs of the undergarments to be stretched when positioning the undergarment on a user to thereby provide a snug and comfortable fit around the legs of a user when relaxed or retracted.

Additionally, folding means 130 is positioned downstream from the combining means 100 for folding each of the plurality of undergarments U of the chain. The folding means, e.g., a folder 130, includes a waistband folder for folding the pair of continuous waistband strips of material forming the waistbands W of the chain. The waistband folder preferably includes waistband guide members which fold portions of the lower non-woven strip which do not have elastic adhered thereto so as now to overlie the upper non-woven strip and lateral peripheries of each individual core. This waistband folder 130 thereby forms both a waistband seal and a smooth inner surface for interfacing with or abuttingly contacting the waist of a user.

The folder 130 also has a core folder positioned downstream from the waistband folder for bi-folding each of the cores C of the plurality of undergarments U of the chain so that the two continuous strips of waistband material are positioned adjacent and in close relation to each other. The core folder, e.g., a first or primary core folder, preferably includes a core folding guide member which abuttingly contacts each of the plurality of individual cores which now have the lengthwise extents thereof travelling in a transverse direction to the path of travel P. The core folder preferably also includes a first compressor positioned downstream from the core folding guide member for compressing the core after it has been folded.

The folder 130 further has an undergarment second core folder, e.g., a side folder, positioned downstream from the core folder for folding each of the bi-folded cores of the plurality of undergarments U of the chain a second time. The side folder, or secondary folder, preferably includes a roller guide member and a belt member cooperating with the roller guide member which guide the lower extending peripheries of the bi-folded core upwardly so as to now be positioned adjacent the waistband strips as illustrated. The side folder preferably also includes a second compressor preferably positioned downstream from the roller guide and the belt member for compressing the core after the second or side fold. Although the side folder is applicable to all type of garments, it is particularly applicable to adult undergarments which generally include cores having a greater lengthwise extent than those for infants or toddlers. The side folder, for example, allows the core to be folded to a more compact position for handling, stacking, and/or packaging further downstream.

Also, side connecting means, e.g., including a side connector 150, is positioned downstream from the folding means 130 for intermittently connecting at least portions of the two continuous strips of waistband material extending between each of the plurality of cores C of the plurality of undergarments U of the chain to form side peripheries of individual undergarments U. The side connecting means 150 preferably includes a registration conveying means, e.g., a registration conveyor 155, positioned downstream from the folding means 140 for receiving, registering, holding or clamping, and conveying the chain of the plurality of undergarments U to and through a side sealer 160 and to second separating means, e.g., a final knife or an undergarment separator 180.

The side sealer 160 of the side connecting means 150 preferably is connected to the frame 25 and is positioned to ultrasonically and connectively seal the intermittent portions of the waistband material of the chain as the undergarments are being conveyed. The side sealer 160 preferably includes a horn assembly having a horn rotatably mounted on the frame 25 along one side of the path of travel P and an anvil assembly rotatably mounted on the other side of the path of travel P and positionally aligned with the horn assembly so as to seal or clamp opposing portions of the waistband strips together for sealing thereof. Examples of such a horn and anvil assembly are illustrate and described in co-pending U.S. patent application Ser. No. 07/884,804 filed on May 19, 1992 and which is hereby incorporated herein by reference. More particularly, the horn assembly and the anvil assembly, according to a first embodiment, are each mounted on a pair of space-apart drive wheels which are pivotally connected to a drive rod. Each of the drive wheels preferably is rotated by a corresponding shaft and gear arrangement, including corresponding gears, with each of the drive gears being driving by a respective pinion. An ultrasonic horn is mounted to a distal end of one drive rod, and an ultrasonic anvil is mounted to the distal end of the other drive rod. The anvil is mounted to a back plate via an air bladder which is capable of being alternately inflated and deflated from an air supply. This construction permits the anvil to be inflated outwardly toward the horn and also imparts a significant degree of flexibility and alignment to the anvil via the air bladder. The anvil preferably is also cooled to reduce glue or adhesive build up in the sealing process.

In operation, rotation of each pair of drive wheels results in the reciprocal movement of the corresponding drive rod toward the chain or web of undergarments. It will be understood by those skilled in the art that with the provision of the inflatable bladder, the anvil is imparted with a significant degree of flexibility or compressibility which thereby permits the horn and the anvil to be in contact with each other for a much greater period of time during movement of the chain through the side sealer along the path of travel P. This results in a much better forming of weld seams in the chain. Additionally, the timing of the application of the horn and anvil preferably is such so as to increase the benefits of the sealing process.

Alternatively, e.g., as an additional embodiment of a side connector, a side connector 160 can include a side connector drive 180 according to the present invention. In this embodiment, the side connector 160 is also an ultrasonic side sealer which includes a horn assembly and anvil assembly. Driving means, e.g., a side connector drive, is preferably connected to the side sealer for driving the side sealer along the path of travel. The drive preferably includes a motor, e.g., a servo-motor as understood by those skilled in the art, connected to the frame 25 and a wheel and a crank assembly connected to the motor. The wheel and crank assembly rotate corresponding to the rotation of a drive shaft and belt connected to the motor. The wheel and crank assembly preferably includes a bar link connected to a wheel and connected to a portion of the side sealer 160 as illustrated. The drive preferably drives the side sealer 160 along the path of travel P, e.g., upstream and downstream, as indicated by the arrows and is preferably controlled and synchronized so that the side sealer 160 is driven downstream at a speed synchronous to the speed of the registration conveyor 155 having the chain of undergarments U positioned thereon.

More particularly, the side sealer 160 of this embodiment has a main support shaft connected to the frame 25 and oriented in the same direction as the path of travel P. A pair of loading cam support shafts also connect to the frame 25 and extend transverse to, e.g., orthogonal, the main support shaft. A main shuttle is slidably mounted to the main support shaft and is connected to the wheel and crank assembly of the drive. Each of the horn and anvil assemblies preferably connect to first and second cams which load and unload or open and close the respective assemblies during operation. The first cam has an air bag, e.g., a loading air bag, connected thereto which assists in turning the first cam on and off by introducing air into the air bag or deflating the air bag as necessary and helps maintain synchronization for a smooth process. The air bags push the first cam against the second cam which preferably runs at about one-half the speed of the corresponding cam wheel, or, in other words, the second cam preferably is a double cam.

To control this portion of the operation, the air supplied to the air bags is regulated by a plurality of regulator valves and solenoid valves, preferably including quick-exhaust functions, positioned in fluid communication with the air bags and an air source. This air control system preferably also controls the separate air bladder or bladders of the anvil assembly as described above with respect to the previous embodiment. As described above herein, by use of the inflatable bladder, the anvil is imparted with a significant degree of flexibility or compressibility which thereby permits the horn and the anvil to be in contact with each other for a much greater period of time during movement of the undergarment chain through the side sealer 160 along the path of travel P. The second cam assists with the opening and closing of the horn and anvil assemblies after the main shuttle speed synchronizes with the clamp conveyor speed. The horn and anvil assemblies are each connected to the second cam and each slidably mount to a pair of spaced-apart assembly support members as illustrated for movement in a direction toward the product as shown by the arrows.

After the main shuttle and the horn and anvil assemblies are positioned upstream and begin to move downstream at a speed synchronized with the clamp conveyor speed, the horn and the anvil close and hold side periphery portions of the waistband material, e.g., pair of waistband material. The assemblies are energized to provide ultrasonic energy to the material positioned between the horn and the anvil. The material melts and the ultrasonic energy is stopped. The horn and anvil, however, remain closed so that the material positioned therebetween will cool and resolidify to thereby form a seal or bond between the pair of waistband material.

The disposable undergarment forming apparatus 20 also includes second separating means, e.g., an undergarment separator 180, is positioned downstream from the side connecting means 160 for separating the connective seal of the portions of the continuous strips of waistband material of the chain into a plurality of individual disposable undergarments U. The second separating means is preferably a final knife fixedly mounted to the frame 25 and arranged to periodically cut the chain of the plurality of undergarments U. It will be understood by those skilled in the art, however, that other undergarment separator 180 configurations, as well as the other separators described herein, could be used as well, including various bade configurations, optical configurations (e.g., laser), and wire-type cutter configurations. The driving means of the side connector preferably is electrically connected to and tracks with or is synchronized with the undergarment separator 180 so that the position and timing for cutting or separating the chain into individual undergarments advantageously occurs at the right time and position on the seal of the waistband material.

Further, the apparatus 20 includes stacking and packaging means 190 is positioned downstream from the undergarment separator 180 for stacking and packaging the individual undergarments U produced. The stacking and packaging means 190 preferably includes position orientating means, e.g., a position orientor, positioned downstream from the second separating means 180 for positionally orienting the plurality of individual undergarments U from a generally vertical orientation to the generally horizontal orientation for side-entry stacking as illustrated. The individual undergarments U are compressed and conveyed by a compression conveyor to a position for stacking. The compression conveyor preferably includes a compression conveying drive, a plurality of compression rolls connected to the drive, and a plurality of belts slidably mounted to the rolls. During the driving of the rolls by the conveying drive, the belts compress and convey the individual undergarments along the path of travel P to the stacking means positioned downstream therefrom.

Side-entry stacking means, e.g., a side-entry stacker, of the stacking and packaging means is positioned downstream from the second separating means 180, the position orienting means, and the registration conveyor for receiving a plurality of individual disposable undergarments U from the generally horizontal side-entry position and for stacking the plurality of disposable undergarments U into a predetermined stack. The side-entry stacker 190 is preferably positioned transverse the path of travel P so as to advantageously provide a shorter linear path of travel and shorter footprint for the apparatus 20. The stacker 190 preferably includes a base and a plurality of space-apart guiding arms rotatably mounted to the base. The side-entry stacker 190 can also include a stop member positioned to stop each of the plurality of compressed undergarments in a predetermined stop position after being conveyed by the registration conveyor. The spaced-apart guiding arms then rotate adjacent the predetermined stop position and individually lift each of the undergarments so that the undergarments are positioned between the guiding arms and transported to a stacker output position which provides stacks of undergarments. The stacker also preferably includes a controller for controlling the rotating guiding arms and for tracking and/or counting the individual undergarments U. The controller also allows an operator to set the number of undergarments to be arranged in the stacks for various sized or types of packaging or bagging.

After the plurality of individual undergarments U are stacked, the stack of undergarments U is compressed by a stacking compressor of the side-entry stacker and conveyed by a packaging conveyor of the stacking and packaging means 190 to a position for packaging or bagging. The packaging or bagging means of the stacking and packaging means 190 preferably includes a loader as understood by those skilled in the art which assists in the bagging of the stack of undergarments U by production process personnel such as designated undergarment baggers.

Preferably, a scrap/reject or bulk receiving source is also positioned between the undergarment separator 180 and the stacking and packaging 190. This scrap/reject or bulk receiving source also provides flexibility in the operation of the apparatus 20 as an outlet for a jam, a line down, or other operational problems that may arise.

Additionally, as an example of an alternative embodiment of the present invention, an apparatus according to the present invention can include leg forming means, e.g., a leg former, positioned downstream from the core forming means for forming a pair of leg openings in each of the plurality of undergarments of the chain. This particular embodiment forms a brief product preferably used by an adult, but can also be used by a toddler. The leg forming means can include layer applying means for applying a continuous layer of non-woven material so as to underlie each of the plurality of individual undergarment cores U, leg elastic applying means positioned downstream from the layer applying means for applying leg elastic between the layer of non-woven material and the waistbands, and leg cutting means positioned downstream from the layer applying means for cutting the pair of leg openings in the layer of non-woven material. The side connecting means 150, e.g., a side sealer 160 as described above herein, according to this second embodiment, further connects the side peripheries of each of the plurality of undergarments from the waistbands, along the side peripheries of the layer of non-woven material, and to each of the pair of leg openings.

As illustrated in FIGS. 1–12, and although other methods are illustrated as well, the present invention advantageously provides methods for orienting a portion of a disposable undergarment such as a core, a waistband, a leg gather, a backing sheet, or respective portions thereof. A method preferably includes lifting a portion of a disposable undergarment by a lifter when in a first orientation position during travel along a predetermined path and orienting the portion of the disposable undergarment in a second orientation position along the predetermined path of travel by driving the lifter along the predetermined path of travel and changing the orientation of the lifted portion of the disposable undergarment to the second orientation position when driving the lifter along the predetermined path of travel.

The method can also advantageously include the orienting step providing first and second driving paths D1, D2. The second driving path D2 is preferably positioned to generally overlie the first driving path D1 and directs the core lifter 72 along a different path of travel than the first driving path D1. THE method additionally can include adjustably compensating the position of the lifter 72 for the differences in the first and second driving paths D1, D2 when the core C is being oriented to the second orientation position.

The method can further include holding the core C in a suspended position after lifting the core C off of a surface, e.g., of the conveyor 71, and releasing the core from the suspended position. The holding step preferably includes applying suction from the core lifter 72 to the core C so as to operatively lift the core C from the surface. Likewise, the releasing step can include disabling the suction from the core lifter 72, e.g., by disengagement of the suctioning interface member 83 with the suction delivery channel 86, so as to inoperatively release the core onto a surface after the core C is oriented in the second desired orientation position.

Because the core of a disposable undergarment can require extensive forming, preparing, and handling operations, e.g., due to the absorbency or super-absorbency nature of the core of a disposable undergarment, the method of the present invention can advantageously be and is preferably used for orienting a core of a disposable undergarment. Accordingly, another method of the present invention preferably includes lifting a core of a disposable undergarment by a core lifter 72 when in a first orientation position during travel along a predetermined path and orienting the core C in a second orientation position along the predetermined path of travel by driving the core lifter 72 along the predetermined path of travel and changing the orientation of the lifted core C to the second orientation position when driving the core lifter 72 along the predetermined path of travel. Additional method steps can also be included as described above with respect to the other method and as illustrated in the drawings.

Further, because it is generally desirable to produce a large plurality, e.g., hundreds, thousands, or tens of thousands, of disposable undergarments rapidly, efficiently, and in a smaller square footage of manufacturing floor space, yet another method for orienting a plurality of cores of a web of disposable undergarments is advantageously provided according to the present invention. Yet another method, as perhaps best illustrated in FIG. 12, preferably includes transporting each of the plurality of cores loaded on the conveyor 71 (Block 210) along a predetermined path of travel when in a first orientation position, lifting or picking up each of the plurality of cores (Block 212) by one of a plurality of lifters 72 after the vacuum head or delivery channel 86 of the vacuum system 82 has been initiated, contacted by the suctioning interface member 83, or turned on (Block 211) when each of the plurality of cores C are in the first orientation position during travel along a predetermined path, and orienting each of the plurality of cores C in a second orientation position (Block 213) along the predetermined path of travel by driving the lifter 72 along the predetermined path of travel and changing the orientation of each of the lifted cores C to the second orientation position when driving each of the plurality of lifters 72 along the predetermined path of travel. The vacuum head or delivery channel 86 is then disengaged by the suctioning interface member 83 (Block 214), and the core C is released onto a surface for combining or positioned for combining with the waistband strips W1, W2 (Block 215). Additional method steps can be included as described above with respect to the other methods and as illustrated in the drawings.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed:

1. An apparatus for orienting a core of a disposable undergarment, the apparatus comprising:

core forming means for forming a plurality of undergarment cores each having a lengthwise extent thereof extending in a selected direction of travel, the selected direction of travel being linear;

core conveying means positioned to receive the plurality of undergarment cores for conveying the plurality of undergarment cores in the selected direction of travel;

lifting means positioned adjacent said core conveying means for lifting a core of a disposable undergarment when in a first orientation position during travel along the selected direction of travel, said lifting means including core holding means for holding a core in a suspended position after lifting the core off a surface of said core conveying means and for releasing the core form the suspended position; and core orienting means connected to said lifting means for orienting the core in a second different orientation position spaced-apart along the selected direction of travel, said core orienting means including driving means for driving said lifting means along the selected direction of travel and orientation changing means associated with said driving means for changing the orientation of the lifted core to the second different orientation position when driving said lifting means along the selected direction of travel.

2. An apparatus as defined in claim 1, wherein said orientation changing means includes means for driving portions of said lifting means along first and second driving paths, the second driving path being positioned to generally overlie the first driving path and to direct a second portion of said lifting means along a different path of travel than a first portion traveling along the first driving path.

3. An apparatus as defined in claim 1, wherein said core holding means includes a suction system for operatively lifting the core from a surface of said core conveying means and for inoperatively releasing the core onto another surface.

4. An apparatus as defined in claim 1, wherein said lifting means includes a plurality of individual core lifters, each of the plurality of individual core lifters having a platen for abuttingly contacting the core during lifting thereof, a first arm connected to said platen and connected to a first portion of said driving means and a second arm connected to said first arm and to a second portion of said driving means, the second portion of said driving means being positioned for driving said second arm along a different path of travel than the first portion of said driving means which drives said first arm along a selected path of travel.

5. An apparatus as defined in claim 4, wherein said first arm of each of the plurality of individual core lifters includes a substantially hollow portion extending a selected length of said first arm, wherein said platen includes a plurality of openings formed therein and positioned in fluid communication with the substantially hollow portion of said first arm connected thereto, and wherein each of said plurality of individual core lifters further includes a suctioning interface member connected to said first arm and in fluid communication with the substantially hollow portion of said first arm so that when suction is applied to the suctioning interface member when each of said plurality of individual core lifters travels along the predetermined path the suction extends through the suctioning interface member, through the substantially hollow portion of said first arm, and through the plurality of openings in said platen for lifting a core when positioned on a surface adjacent said platen.

6. An apparatus as defined in claim 5, wherein said lifting means further includes an elongate suction delivery channel positioned in a plane overlying said core conveying means for interfacing with each of said suction interface members for delivering suction thereto as each of the plurality of individual core lifters travel along the selected direction of travel.

7. An apparatus as defined in claim 6, wherein each of the plurality of individual core lifters are driven by said driving means along the selected direction of travel adjacent said core conveying means so that each of the plurality of individual core lifter only lift and release a core only when positioned adjacent said core conveying means.

8. An apparatus as defined in claim 6, wherein said first arm is fixedly connected to the first portion of said driving means, and wherein said second arm of each of said plurality of individual core lifters is rotatably connected to said first arm and slidably connected to the second portion of said driving means.

9. An apparatus as defined in claim 8, wherein each of said individual core lifters further includes a pin connected to the second portion of said driving means and slidably connected to said second arm, said second arm including an elongate slot positioned to receive the pin therein so that the pin slidingly travels along the length of the elongate slot.

10. An apparatus as defined in claim 6, wherein each of said plurality of individual core lifters continuously travel along a closed loop path of travel when being driven by said driving means.

11. An apparatus as defined in claim 1, wherein the selected direction of travel is in a linear direction, wherein the first position of orientation of the core has the lengthwise extent of the core oriented in the same direction as the predetermined path of travel, and wherein said core orienting means orients the lengthwise extent of the core so that the lengthwise extent of the core is then transverse the selected direction of travel in the same linear direction.

12. An apparatus as defined in claim 1, wherein said driving means includes at least a pair of closed-loop chains, a plurality of gears for contactingly driving each of the pairs of chains, and at least one motor for driving each of the plurality of gears.

13. An apparatus as defined in claim 11, wherein said core conveying means is positioned downstream from core forming means and upstream from waistband/core combining means so that the oriented core is positioned to connect to an undergarment waistband.

14. An apparatus for orienting a plurality of cores of web of a plurality of disposable undergarments, the apparatus comprising:

lifting means for lifting each of a plurality of cores of a disposable undergarment when in a first orientation position during travel along a selected direction of travel, said lifting means including a core holding means for holding each of the plurality of cores in a suspended position after lifting each of the cores off of a surface and for releasing each of the plurality of cores from the suspended position, the selected direction of travel being linear;

core orienting means connected to said lifting means for orienting each of the plurality of cores in a second different orientation position spaced-apart along the selected direction of travel, said core orienting means including driving means for driving said lifting means along the selection direction of travel and orientation changing means associated with said driving means for changing the orientation of each of the lifted cores to the second different orientation position when driving said lifting means along the selected direction of travel; and waistband/core combining means positioned downstream from said lifting means and said core orienting means for combing each of the plurality of spaced-apart cores with at least a pair of spaced-apart, elongate strips of waistband material to thereby form a web of a plurality of disposable undergarments.

15. An apparatus as defined in claim 14, wherein said orientation changing means includes means for driving portions of said lifting means along first and second driving paths, the second driving path being positioned to generally overlie the first driving path and to direct a second portion of said lifting means along a different path of travel than a first portion traveling along the first driving path.

16. An apparatus as defined in claim 14, wherein said core holding means includes a suction system for operatively lifting each of the cores from a surface and for inoperatively releasing each of the cores onto a surface.

17. An apparatus as defined in claim 14, wherein said lifting means includes a plurality of individual core lifters, each of the plurality of individual core lifters having a platen for abuttingly contacting one of the plurality of cores during lifting thereof, a first arm connected to said platen and connected to a first portion of said driving means and a second arm connected to said first arm and to a second portion of said driving means, the second portion of said driving means being positioned for driving said second arm along a different path of travel than the first portion of said driving means which drives said first arm along a selected path of travel.

18. An apparatus as defined in claim 17, wherein said first arm of each of the plurality of individual core lifters includes a hollow portion extending a selected length of said first arm, wherein said platen includes a plurality of openings formed therein and positioned in fluid communication with the hollow portion of said first arm connected thereto, and wherein each of said plurality of individual core lifters further includes a suctioning interface member connected to said first arm and in fluid communication with the hollow portion of said first arm so that when suction is applied to the suctioning interface member when each of said plurality of individual core lifters travels along the selected direction of travel the suction extends through the suctioning interface member, through the hollow portion of said first arm, and through the plurality of openings in said platen for lifting one of the plurality of cores when positioned on a surface adjacent said platen.

19. An apparatus as defined in claim 18, further comprising core conveying means having at least portions positioned upstream from said lifting means for conveying the plurality of individual undergarment cores along the selected path of travel, and wherein said lifting means further includes an elongate suction delivery channel positioned in a plane overlying said core conveying means for interfacing with each of said suction interface members for delivering suction thereto as each of the plurality of individual core lifters travel along the selected direction of travel.

20. An apparatus as defined in claim 19, wherein each of the plurality of individual core lifters are driven by said driving means along the selected direction of travel adjacent said core conveying means so that each of the plurality of individual core lifters only lift and release one of the plurality of cores only when positioned adjacent said core conveying means.

21. An apparatus as defined in claim 20, wherein said first arm is fixedly connected to the first portion of said driving means, and wherein said second arm of each of said plurality of individual core lifters is rotatably connected to said first arm and slidably connected to the second portion of said driving means.

22. An apparatus as defined in claim 21, wherein each of said individual core lifters further includes a pin connected to the second portion of said driving means and slidably connected to said second arm, said second arm including an elongate slot positioned to receive the pin therein so that the pin slidingly travels along the length of the elongate slot.

23. An apparatus as defined in claim 22, wherein each of said plurality of individual core lifters continuously travel along a closed loop path of travel when being driven by said driving means.

24. An apparatus as defined in claim 23, wherein the selected direction of travel is in a linear direction, wherein the first position of orientation of the core has the lengthwise extent of the core oriented in the same direction as the selected direction of travel, and wherein said core orienting means orients the lengthwise extent of the core so that the lengthwise extent of the core is then transverse the selected direction of travel in the same linear direction.

25. An apparatus as defined in claim 24, wherein said driving means includes at least a pair of closed-loop chains, a plurality of gears for contactingly driving each of the pair of chains, and at least one motor for driving each of the plurality of gears.

26. An apparatus for orienting a portion of a disposable undergarment, the apparatus comprising:

a disposable undergarment conveyor positioned to convey a plurality of portions of a disposable undergarment along a selected direction of travel in a linear direction;

a plurality of lifters each positioned to lift a portion of a disposable undergarment when in a first orientation position of a disposable undergarment when in a first orientation position from said conveyor during travel along the selected direction of travel, each of said plurality of lifter includes holding means for holding the portion of the disposable undergarment in a suspended position after lifting the portion off of a surface of said disposable undergarment conveyor and for releasing the portion from the suspended position; and an orientor connected to said plurality of lifters for orienting the portion of the disposable undergarment in a second different orientation position spaced-apart along the same selected direction of travel in the linear direction, said orientor including at least one drive for driving said plurality of lifters along the selected direction of travel and an orientation changer associated with said at least one drive for changing the orientation of the lifted portion of the disposable undergarment to the second orientation position when driving said plurality of lifters along the selected direction of travel.

27. An apparatus as defined in claim 26, wherein said orientation changer includes means for driving portions of each of said plurality of lifters along first and second driving paths, the second driving path being positioned to generally overlie the first driving path and to direct a second portion of each of said plurality of lifters along a different path of travel than a first portion traveling along the first driving path.

28. An apparatus as defined in claim 26, wherein said holding means includes a suction system for operatively lifting the portion of the disposable undergarment from a surface and for inoperatively releasing the portion onto a surface.

29. An apparatus as defined in claim 26, wherein each of said plurality of lifters includes a platen for abuttingly contacting the portion of the disposable undergarment during lifting thereof, a first arm connected to said platen and connected to a first portion of said at least one drive and a second arm connected to said first arm and to a second portion of said at least one drive, the second portion of said at least one drive being positioned for driving said second arm along a different path of travel than the first portion of said at least one drive which drives said first arm along a selected path of travel.

30. An apparatus as defined in claim 29, wherein said first arm of each of the plurality of lifters includes a hollow portion extending a selected length of said first arm, wherein said platen includes a plurality of openings formed therein and positioned in fluid communication with the hollow portion of said first arm connected thereto, and wherein each of said plurality of lifters further includes a suctioning interface member connected to said first arm and in fluid communication with the hollow portion of said first arm so that when suction is applied to the suctioning interface member when each of said plurality of individual lifters travels along the selected direction of travel the suction extends through the suctioning interface member, through the hollow portion of said first arm, and through the plurality of openings in said platen for lifting a portion of the disposable undergarment when positioned on a surface adjacent said platen.

31. An apparatus as defined in claim 30, further comprising an elongate suction delivery channel positioned in a plane overlying said conveyor for interfacing with each of said suction interface members of said plurality of lifters for delivering suction thereto as each of the plurality of lifters travel along the selected direction of travel.

32. An apparatus as defined in claim 31, wherein each of the plurality of lifters are driven by said at least one drive along the selected direction of travel adjacent said conveyor so that each of the plurality of individual lifters only lift and release a portion of a disposable undergarment only when positioned adjacent said conveyor.

33. An apparatus as defined in claim 31, wherein said first arm is fixedly connected to the first portion of said at least one drive, and wherein said second arm of each of said plurality of lifters is rotatably connected to said first arm and slidably connected to the second portion of said at least one drive.

34. An apparatus as defined in claim 33, wherein each of said plurality of lifters further includes a pin connected to the second portion of said driving means and slidably connected to said second arm, said second arm including an elongate slot positioned to receive the pin therein so that the pin slidingly travels along the length of the elongate slot.

35. An apparatus as defined in claim 31, wherein each of said plurality of lifters continuously travels along a closed loop path of travel when being driven by said at least one drive.

36. An apparatus as defined in claim 26, wherein the first position of orientation of the portion of a disposable undergarment has the lengthwise extent thereof oriented in the same direction as the selected direction of travel, and wherein said orienter orients the lengthwise extent of the disposable undergarment portion so that the lengthwise extent of the disposable undergarment portion is then transverse the selected direction of travel.

37. An apparatus as defined in claim 26, wherein said at least one drive includes at least a pair of closed-loop chains, a plurality of gears for contactingly driving each of the pair of chains, and at least one motor for driving each of the plurality of gears.

38. An apparatus as defined in claim 31, wherein said conveyor is positioned downstream from disposable undergarment portion forming means which is positioned for forming a plurality of portions of a disposable undergarment and upstream from combining means so that the oriented disposable undergarment portion is positioned to connect to another portion of a disposable undergarment.

* * * * *

UNITED STATES PATENT AND TRADEMARK OFFICE
CERTIFICATE OF CORRECTION

PATENT NO. : 6,116,317
DATED : September 12, 2000
INVENTOR(S) : Tharpe, Jr. et al.

It is certified that error appears in the above-identified patent and that said Letters Patent is hereby corrected as shown below:

| | |
|---|---|
| Column 1, Line 23 | Delete "sized" and insert - -sizes- - therefor. |
| Column 2, Line 4 | Delete "form" and insert - -from- - therefor. |
| Column 5, Line 24 | Delete "form and" and insert - -from an- - therfor. |
| Column 10, Line 19 | Delete "from" and insert - -form- - therefor. |
| Column 10, Line 29 | Delete "space-apart" and insert - -spaced-apart- - therefor. |
| Column 11, Line 24 | Delete "type" and insert - -types- - therefor. |
| Column 11, Line 56 | Delete "illustrate" and insert - - illustrated- - therefor. |
| Column 13, Line 36 | Delete "bade" and insert - -blade- - therefor. |
| Column 16, Line 35 | Delete "form" and insert - -from- - therefor. |

UNITED STATES PATENT AND TRADEMARK OFFICE
CERTIFICATE OF CORRECTION

PATENT NO. : 6,116,317
DATED : September 12, 2000
INVENTOR(S) : Tharpe, Jr. et al It is certified that error appears in the above-identified patent and that said Letters Patent is hereby corrected as shown below:

Column 18, Line 15    Delete "selection" and insert - -selected- - therefor.

Column 18, Line 23    Delete "combing" and insert - -combining- - therefor.

Signed and Sealed this

Twenty-fourth Day of April, 2001

Attest:

NICHOLAS P. GODICI

*Attesting Officer*    *Acting Director of the United States Patent and Trademark Office*